United States Patent [19]

Harris et al.

[11] Patent Number: 5,055,456
[45] Date of Patent: Oct. 8, 1991

[54] ANTI-ALOPECIA COMPOSITION

[75] Inventors: Bruce J. Harris, Markham, Canada; James R. Lawter, Orange; Lawrence Ritter, Rockland, both of N.Y.

[73] Assignee: American Cyanamid Co., Stamford, Conn.

[21] Appl. No.: 302,813

[22] Filed: Jan. 27, 1989

[51] Int. Cl.$^5$ .............................................. A61K 31/20
[52] U.S. Cl. ...................................... 514/57; 424/70; 514/159; 514/164; 514/880; 514/881; 514/946; 514/947
[58] Field of Search ................ 514/57, 159, 164, 880, 514/881, 946, 947; 424/70

[56] References Cited

U.S. PATENT DOCUMENTS

| | | | |
|---|---|---|---|
| 4,126,142 | 11/1978 | Saute | 424/78 |
| 4,199,576 | 4/1980 | Reller et al. | 514/159 |
| 4,470,965 | 9/1984 | Wolf et al. | 424/80 |
| 4,849,227 | 7/1989 | Cho | 424/456 |
| 4,874,791 | 10/1989 | Adachi et al. | 514/880 |

OTHER PUBLICATIONS

Cosmetics Toiletries, vol. 95, Jul. 1980, pp. 51–54, "A New Cosmetic Fluid Emollient for Use in Antiperspirants".

*Primary Examiner*—Ronald W. Griffin
*Attorney, Agent, or Firm*—Robert P. Raymond

[57] ABSTRACT

This invention is concerned with a composition of matter and method of applying same for use as hair grooming aid or preferably, to treat androgenetic alopecia comprising (a) an effective amount of a polysaccharide or mixtures thereof, polysaccharide derivatives or mixtures thereof, or any combination of the foregoing; and (b) a minor amount of a fatty acid ester of sorbitol and its anhydrides, or mixture of said fatty acid esters; and (c) a minor amount of a lower alkyl ester of p-hydroxy benzoic acid or mixture of said esters; and (d) water sufficient to create a composition of 100% by volume.

11 Claims, No Drawings

ANTI-ALOPECIA COMPOSITION

BACKGROUND OF THE INVENTION

Hair growth is not continuous but rather cyclic, with alternating periods of growth 'anagen' and rest 'telogen'. In the scalp, the anagen phase lasts about 6 years and the telogen phase about 4 months. The growth of scalp hair is not synchronous, and the rate of growth is about 0.4 mm per day. About 90 percent of the more than 100,000 scalp hairs are growing (anagen), so that 50 to 100 hairs are shed daily as they are pushed out at the onset of a new hair cycle. These telogen hairs are also called club hairs because their ends are surrounded by visible clumps of keratinized cells.

The human skin has two kinds of hair. The terminal hairs are long, thick, and pigmented, while the vellus hairs are short, thin, and poorly pigmented. The terminal hairs can be easily seen with the unaided eye (scalp, beard, etc.) while the vellus hairs are only readily visible with magnification.

Common baldness is seen in the vast majority of adult males and is considered physiologic and part of the aging process. Since the degree, intensity, and age of onset of hair loss shows marked individual variations the most severe cases require the reassurance and understanding of the physician. Although several patterns of common baldness have been described in males, the recession of the hair line in the frontal region is by far the most common early finding. Eventually, alopecia develops on the vertex and as the two borders of alopecia advance, a semilunar configuration of hair loss develops. Besides the loss of hair, the length and diameter of each hair will be reduced in the adjacent areas even though the follicles remain intact.

In women, on the other hand, androgenetic alopecia is characterized by diffuse thinning over the vertex, parietal and temporal regions, but there is normal retention of the frontal hair line and the occipital zone is spared.

The cause of baldness is not well-established but a multifactorial form of inheritance has been suggested, which means that the loss is the result of the interaction of several genes with environmental factors. Genetically predisposed hair follicles seem to become the target for androgenic hormones and these follicles are programmed to become progressively smaller in size and to have shorter periods of growth. In the end stage only fine vellus hairs remain. It is not known how the androgens work or even whether the target tissue is the hair bulb or the supporting dermal components. There is no difference, for example, in the excretion of 17-ketosteroids or the blood levels of testosterone between normal balding and nonbalding individuals. The clinical difference between male and female pattern baldness is probably a function of the female genes, since it is believed that the same pathogenic mechanism applies to both.

Androgenetic alopecia can be distinguished from several other varieties of alopecia by etiologic diagnosis.

Telogen effluvium is a transient, reversible, diffuse shedding of hair in which a high percentage of hair follicles enter the telogen phase prematurely as a result of physical or mental illness. Among the most important factors incriminated are childbirth, high fever, hemorrhage, sudden starvation, accidental or surgical trauma, severe emotional stress, and certain drugs.

The diffuse shedding of telogen effluvium is not apparent for 2 to 3 months after the traumatic event and for that reason it is important to investigate in the history the above factors since the patient is usually unaware of the relationship. Although the hair loss is usually not excessive or prolonged enough to produce thinning of hair, in specific instances when the insult is prolonged thinning may become clinically apparent.

Alopecia areata is an immunologic alopecia characterized by the abrupt onset of sharply defined areas of hair loss. In mild cases, the process can be discovered accidentally by hairdressers or other persons examining the scalp of a patient, since hair loss can be clinically evident. In more severe cases, the patient may complain of excessive shedding of hair with large areas of the scalp completely devoid of hair. In the most severe cases, the scalp will develop total hair loss (alopecia totalis) or the hair loss will involve the whole body surface (alopecia universalis).

Although the disease affects any age, the higher incidence occurs in younger persons in whom 33 percent of the cases start by age 20. Only 25 percent of affected patients are over 40 years of age. There is no sex preference. Familial occurrence is between 10 and 20 percent and a familial tendency seems to be associated with a worse prognosis.

Most of the patients will run an unpredictable and relapsing course with multiple episodes of hair loss and regrowth. Only about 20 to 30 percent will have a single reversible episode. Regrowth of hair is common within several months, but in many instances is not complete and relapses are common.

Alopecia areata may be associated with autoimmune diseases such as vitiligo, pernicious anemia, collagen disease, and endocrinopathies. The characteristic histologic changes suggest an autoimmune etiology, but immunofluorescence studies have not revealed any evidence of bound antibody and no circulating antibodies to hair follicles have been demonstrated.

Traumatic alopecia is induced by physical trauma, of which the two most important groups, from the therapeutic standpoint are trichotillomania and alopecia resulting from cosmetic procedures or improper hair care. Trichotillomania is a compulsive habit in which the individual repeatedly pulls or breaks off his or her own hair in a partially conscious state similar to thumb sucking or nail biting. Clinically, this form of alopecia is characterized by an ill-defined patch on which the hairs are twisted and broken at various distances from the scalp surface. The scalp and hairs look otherwise normal. Other hairy areas of the body like the eyebrows and pubic region can be targets for this type of manipulation.

Traumatic alopecia from cosmetic procedures is done consciously in ill-advised individuals and is almost exclusively seen among females. The clinical pattern in these cases will be dictated by the different types of manipulation performed and it requires the suspicion of the observer. For example, traction alopecia from hair strengtheners and from brushes with synthetic fibers may produce alopecia in the temporofrontal regions, while traction alopecia from combs and rollers could affect the vertex and parietal regions. Sometimes this type of alopecia is associated with folliculitis induced by the occlusive effect of the oily cosmetics used in the procedure.

Anagen effluvium is a temporary alopecia caused by the inhibition of mitosis in the hair papilla by certain cytotoxic drugs, leading to constriction of the hair shaft or to complete failure of hair formation. The narrow hair shaft breaks easily and produces a characteristic pattern of tapered hairs that uniformly fracture at the same distance from the skin surface. Typically this effect will be evident from 10 days to 6 weeks after the administration of the cytotoxic agent and will resolve gradually upon discontinuation of the medication. Treatment is not necessary, but the patient should be apprised of the problem.

Alopecia may also result from nutritional deficiencies and metabolic defects. Caloric deprivation must be very severe to produce hair loss. Increased shedding sometimes occurs after marked weight loss for obesity. Anemia, diabetes, hyper- and hypovitaminosis, and zinc deficiency may also lead to alopecia.

Unfortunately, treatment for androgenetic alopecia has been ineffective in inducing regrowth. The use of cyclic estrogen therapy in females with an estrogen-dominant contraceptive or topical estrogen has been advocated to reduce the rate of hair loss, but results are not impressive. The claim that topical testosterone induces the growth of terminal hairs in bald scalp of males has not been confirmed.

In Europe, cyproterone acetate, an antiandrogen chemical that blocks the binding of testosterone by target-cell receptors, has been used combined with ethinylestradiol in females with androgenetic alopecia and found to reduce the rate of telogen shedding and stimulate more regrowth of terminal hairs. It seems that until the effectiveness of this treatment is finally assessed, the side effects and risks (dysmenorrhea, breast tenderness, headache, decreased libido, hepatitis, thrombophlebitis) outweigh its therapeutic effects.

Hair transplants have been used for several years as a corrective procedure for balding men based on the principle that the hair follicles on the occipital region are not under the same influence of androgens as the follicles in the balding area and once transplated will retain the capability of growth. It is a tedious and expensive procedure that requires the expertise of a skilled physician and the motivation and tolerance of the patient. This treatment is usually not indicated for females with androgenetic alopecia, since the loss of hair is too diffuse.

There have been some indications that minoxidil (Rogaine®, Upjohn), a potent vasodilator, has been effective in causing scalp hair regrowth in patients with androgenetic alopecia, but the results have been mixed.

This invention relates to a composition of matter, and a method for applying same, useful as a hair grooming aid and as an effective method in the treatment of androgenetic alopecia.

SUMMARY OF THE INVENTION

According to the present invention there are provided compositions of matter comprising:

a) a minor amount of a polysaccharide or mixtures thereof, polysaccharide derivatives or mixtures thereof; or any combination of the foregoing;

b) a minor amount of a fatty acid ester of sorbitol and its anhydrides or a mixture of said fatty acids esters;

c) a minor amount of a lower alkyl ester of p-hydroxy benzoic acid or a mixture thereof; and d) water qs to 100%.

Generally from about 0.1 to about 1% and preferably from about 0.2 to about 0.5% by weight of (a) may be employed; from about 0.01 to about 0.75%, and preferably from about 0.05 to about 0.25% by weight of (b) may be employed; and from about 0.01 to about 0.5%, preferably from about 0.05 to about 0.25% by weight of a mixture of (c) may be employed.

The invention further contemplates a method for treating androgenetic alopecia said method comprising applying said dermatologic preparation topically to the affected area of the scalp followed by massaging said affected area sufficiently to cause said preparation to penetrate the skin so as to contact the affected hair follicles.

The composition of matter contemplated by the present invention is also useful as a hair grooming aid.

DETAILED DESCRIPTION OF THE INVENTION

Although useful as a hair grooming aid, the invention is broadly applicable to baldness in general, the above defined composition of matter may be especially useful for the treatment of androgenetic alopecia. It has been postulated that an accumulation of materials such as 5-α-dihydro testosterone, a tissue active androgen, in some scalp hair follicles over time causes the regression of hair growth in such follicles. Without being bound by any theory of operation, it is believed that local application of said composition to the skin of the affected area which has been shown to result in renewed growth (Tables I-V), may remove excess androgen.

The skin is ideally suited for topical therapy and at least when it is primarily implicated in the disease, as in androgenetic alopecia, and it would seem the logical route of administration. But topical treatment is not always satisfactory.

Creams are convenient since to some extent they can be used for either dry or wet surfaces, and have the advantage over ointments of being clean to use.

In a preferred embodiment, the composition of matter of this invention comprises preparations which contain polysaccharides, especially polysaccharides of glucose, with a number average molecular weight of between about 250,000 and about 1,000,000; cellulose and its derivatives being preferred.

Special mention is made of compositions which comprise about 0.30% by weight of Sodium carboxymethyl cellulose, about 0.10% by weight of Polysorbate 20, about 0.08 % by weight of methylparaben, about 0.02 % by weight of propylparaben per 100% by volume of purified water.

Preferred component (a), Sodium carboxymethyl cellulose (CMC), such as Cellolax®, is a water soluble cellulose ether prepared by treating alkali cellulose with sodium chloroacetate. This component may be present in amounts from about 0.1 to about 1%, and preferably from about 0.2 to about 0.5% by weight of the entire composition.

Preferred component (b), Polysorbate 20, poly(oxy-1,2-ethanediol) sorbitan mono-9-octadecanoate, is a viscous liquid which is very water soluble. This component may be present in amounts from about 0.01 to about 0.75% and preferably from about 0.05 to about 0.25% by weight of the entire composition.

Preferred component (c) preferably comprises methylparaben (p-methyl benzoic acid) or propylparaben (p-propyl benzoic acid), which are common alkyl esters of p-hydroxy benzoic acid, or mixtures thereof. This component may be present in amounts from about 0.01% to about 0.5% and preferably from about 0.05 to about 0.25% by weight of the entire composition.

The composition of the present invention may be applied topically to the affected area of the scalp in equal divided doses of from about 0.01 ml to about 5 ml, preferably about 0.05 ml to about 2.5 ml and especially preferably from about 0.1 ml to about 1 ml.

A clinical study using the composition of matter of the present invention was undertaken to test the effectiveness of the dermatological preparation in healthy male volunteers, aged 18-65 with vertex baldness and some recession of front hairline common to androgenetic alopecia.

DESCRIPTION OF THE PREFERRED EMBODIMENTS

The invention will be more fully described by the following, non-limiting, examples.

EXAMPLE 1

The above described formulation is prepared as follows:

Approximately 55,000 ml of purified water is chilled to a 4°-6° C. and added to a glass lined jacketed kettle equipped with a propellor type agitator. A 495 g portion of sodium carboxymethylcellulose is added with vigorous agitation to the purified water. This mixture is stirred for 30 minutes or until a clear solution results. A 100,000 ml portion of purified water at 60°-80° C. is added and the mixture is stirred for 10 minutes. A 165 g portion of polysorbate 20 is dissolved in 1000 ml of purified water and added to the mixture. The 132 g of methylparaben and 33 g of propylparaben are added, the temperature of the mixture is raised to 85°-90° C. and the mixture is stirred for 20 minutes or until dissolved. The mixture is cooled to 25°-30° C., the volume adjusted to 165,000 ml with purified water and stirred for 5 minutes. The mixture is then filled into suitable contains.

EXAMPLE 2

The procedure of Example 1 is repeated substituting an equivalent amount of diethylaminoethylcellulose for carboxymethylcellulose.

EXAMPLE 3

The procedure of Example 1 is repeated substituting an equivalent amount of polysorbate 80 for polysorbate 20.

Clinical studies were performed using the formula of Example 1:

|  | % w/v |
|---|---|
| Sodium carboxymethylcellulose | 0.30 |
| Polysorbate 20 | 0.10 |
| Methylparaben | 0.08 |
| Propylparaben | 0.02 |
| Purified Water qs | 100 |

Healthy male volunteers, aged 18-65 with vertex baldness and some recession of front hairline were used. There were several hundred subjects and 23 observing dermatologists. Each subject applied two 0.3 ml portions of the above preparation to the balding areas of their scalp. The duration of treatment was 48 weeks. The primary efficacy parameter was manual hair counts of template area of the subject's scalp. While a variety of parameters were taken into account, the overall mean nonvellus hair counts increased steadily throughout the study with, for example, a raw mean change from baseline of 67.8 hairs at 24 weeks.

The following Tables and Graphs show the changes from baseline obtained in this study based on the indicated influence parameters.

TABLE I

| Raw Change from Baseline (Composite Data) | |
|---|---|
| Week | % Increase in Hair Count |
| 8 | 13 |
| 16 | 24 |
| 24 | 25 |
| 32 | 34 |

TABLE II

Percentage of Subjects who Achieved the Specified change from the Baseline in Nonvellus Hair Count by Time on Treatment

| Change in Hair Count | No. of Subjects (% Subject) | | | |
|---|---|---|---|---|
|  | 8 weeks | 16 weeks | 24 weeks | 32 weeks |
| ≦0 | 110(30%) | 83(25%) | 50(19%) | 21(20%) |
| 0 < Δ ≦ 50 | 145(39%) | 105(32%) | 77(30%) | 22(21%) |
| 50 < Δ ≦ 100 | 66(18%) | 60(18%) | 65(25%) | 24(23%) |
| 100 < Δ ≦ 150 | 26(7%) | 41(12%) | 32(12%) | 18(17%) |
| 150 < Δ ≦ 200 | 12(3%) | 21(6%) | 9(3%) | 4(4%) |
| 200 < Δ ≦ 300 | 13(3%) | 15(5%) | 15(6%) | 9(8%) |
| 300 < Δ ≦ 400 | 0 | 3(1%) | 6(2%) | 2(2%) |
| 400 < Δ ≦ 500 | 0 | 1(0%) | 4(2%) | 2(2%) |
| >500 | 0 | 0 | 1(0%) | 1(1%) |

TABLE III

Summary of Nonvellus Hair Count, Raw Mean Change from Baseline by Time on Treatment and Type of Baldness

| Type of Baldness/Weeks on Treatment | Number | Mean Change |
|---|---|---|
| Type III Vertex | | |
| 8 weeks | 109 | 35.6 |
| 16 weeks | 100 | 59.5 |
| 24 weeks | 78 | 96.0 |
| 32 weeks | 35 | 93.8 |
| Type IV | | |
| 8 weeks | 120 | 25.4 |
| 16 weeks | 111 | 55.0 |
| 24 weeks | 96 | 70.1 |
| 32 weeks | 40 | 81.2 |
| Type V | | |
| 8 weeks | 113 | 26.6 |
| 16 weeks | 106 | 32.9 |
| 24 weeks | 82 | 42.5 |
| 32 weeks | 27 | 65.9 |

TABLE IV

Summary of Nonvellus Hair Count, Raw Mean Change from Baseline by Time on Treatment and Age Group

| Age Category/Weeks on Treatment | Number | Mean Change |
|---|---|---|
| ≦25 Years | | |
| 8 weeks | 21 | 24.6 |
| 16 weeks | 16 | 21.7 |
| 24 weeks | 12 | 70.9 |
| 32 weeks | 5 | 63.2 |
| 26 ≦ Years ≦ 35 | | |
| 8 weeks | 140 | 28.1 |
| 16 weeks | 114 | 49.3 |
| 24 weeks | 92 | 74.9 |
| 32 weeks | 39 | 70.4 |
| 36 ≦ years ≦ 45 | | |
| 8 weeks | 171 | 33.9 |
| 16 weeks | 160 | 51.2 |
| 24 weeks | 124 | 68.6 |
| 32 weeks | 47 | 99.1 |

TABLE IV-continued

Summary of Nonvellus Hair Count, Raw Mean Change from Baseline by Time on Treatment and Age Group

| Age Category/Weeks on Treatment | Number | Mean Change |
|---|---|---|
| ≧46 years | | |
| 8 weeks | 40 | 15.7 |
| 16 weeks | 39 | 37.4 |
| 24 weeks | 31 | 42.3 |
| 32 weeks | 12 | 54.2 |

TABLE V

Summary of Nonvellus Hair Count. Raw Mean Change Baseline by Time on Treatment and Number of Years of Baldness

| Years of Baldness/Weeks on Treatment | Number | Mean Change |
|---|---|---|
| <3 years | | |
| 8 weeks | 162 | 38.3 |
| 16 weeks | 135 | 55.1 |
| 24 weeks | 100 | 84.3 |
| 32 weeks | 38 | 90.9 |
| 3-6 years | | |
| 8 weeks | 156 | 24.0 |
| 16 weeks | 144 | 44.7 |
| 24 weeks | 122 | 61.6 |
| 32 weeks | 51 | 81.0 |
| >6 years | | |
| 8 weeks | 54 | 17.3 |
| 16 weeks | 50 | 34.7 |
| 24 weeks | 37 | 43.7 |
| 32 weeks | 14 | 55.6 |

Many variations of this invention will occur to those skilled in the art in light of the above detailed description. For example, Spans or Tweens or mixtures thereof may be substituted for the emulsifying component (b); instead of methylparaben and propylparaben, ethylparaben may be used as a mold inhibiting stabilizer. All such obvious variations are within the full intended scope of the claims.

What is claimed is:

1. A method for treating androgenetic alopecia in humans, said method comprising applying to the affected areas of the scalp a composition comprising:
    a) an effective amount of a polysaccharide or mixtures thereof, a polysaccharide derivative or mixtures thereof, or any combination of the foregoing;
    b) a minor amount of a fatty acid ester of sorbitol and its anhydrides or a mixture of said fatty acid esters;
    c) a minor amount of a lower alkyl ester of p-hydroxy benzoic acid or mixture of said esters; and
    d) water q.s to 100% by volume.
2. A method as defined in claim 1 wherein component (a) comprised a polysaccharide with a number average molecular weight of between about 250,000 and about 1,000,000.
3. A method as defined in claim 1 wherein component (a) comprises carboxymethylcellulose.
4. A method as defined in claim 3 wherein the carboxymethylcellulose is present in an amount of about 0.30% by weight.
5. A method as defined in claim 1 wherein component (b) comprises polysorbate 20.
6. A method as defined in claim 5 wherein the polysorbate 20 is present in an amount of about 0.10% by weight.
7. A method as defined in claim 1 wherein component (c) comprises a mixture of methylparaben and propylparaben.
8. A method as defined in claim 7 wherein the methylparaben is present in an amount of about 0.08%.
9. A method as defined in claim 1 wherein said composition is applied in equal divided doses of from about 0.01 ml to about 5 ml.
10. A method as defined in claim 9 wherein said composition is applied in equal divided doses of from about 0.05 ml to about 2.5 ml.
11. A method as defined in claim 10 wherein said composition is applied in equal divided doses of from about 0.1 ml to about 1 ml.

* * * * *